United States Patent
Lange

[11] Patent Number: 6,123,706
[45] Date of Patent: Sep. 26, 2000

[54] APPARATUS FOR STABILIZING CERTAIN VERTEBRAE OF THE SPINE

[76] Inventor: Robert Lange, 39 Rue du Temple, F-75004 Paris, France

[21] Appl. No.: 09/213,150

[22] Filed: Dec. 17, 1998

[30] Foreign Application Priority Data

Dec. 17, 1997 [EP] European Pat. Off. ............ 97810998

[51] Int. Cl.[7] ................................................. A61B 17/56
[52] U.S. Cl. ............................................. 606/61; 606/73
[58] Field of Search .......................... 606/61, 73

[56] References Cited

U.S. PATENT DOCUMENTS

| | | |
|---|---|---|
| 4,369,769 | 1/1983 | Edwards . |
| 4,433,676 | 2/1984 | Bobechko . |
| 4,653,481 | 3/1987 | Howland et al. . |
| 5,030,220 | 7/1991 | Howland . |
| 5,613,968 | 3/1997 | Lin .............................................. 606/61 |
| 5,938,663 | 8/1999 | Petreto ....................................... 606/61 |

FOREIGN PATENT DOCUMENTS

| | | |
|---|---|---|
| 0 384 001 | 8/1990 | European Pat. Off. . |
| 0 408 489 | 1/1991 | European Pat. Off. . |
| 2 702 361 | 9/1994 | France . |
| 2 720 923 | 12/1995 | France . |
| 2 730 155 | 8/1996 | France . |
| 195 12 709 | 10/1996 | Germany . |

*Primary Examiner*—Michael Buiz
*Assistant Examiner*—Julian W. Woo
*Attorney, Agent, or Firm*—Browdy and Neimark

[57] ABSTRACT

An improved support system for stabilizing the spine (A) for surgical treatment or other spinal problems which necessitates a fixation of the spinal components (B, C). The system includes a smooth spinal rod (30), at least two connectors 14 slidable along said rod (30), at least two pedicle screws (12) for fixation to a healthy pedicle bone (B, C) on either side of the vertebrae to be repaired, and a one-piece clamping member (14) connecting said pedicle screws (12) to said rod (30) and supporting said connector (14) for limited pivoting movement with respect to the screws (12) and accurate positioning of said rod (30) with respect to the pedicle screws (12).

12 Claims, 5 Drawing Sheets

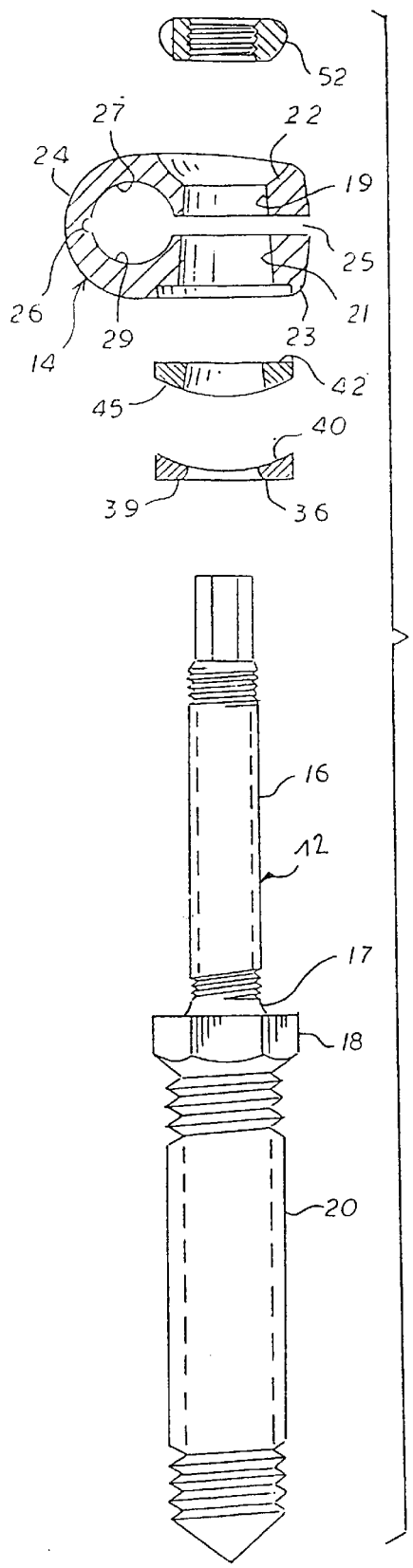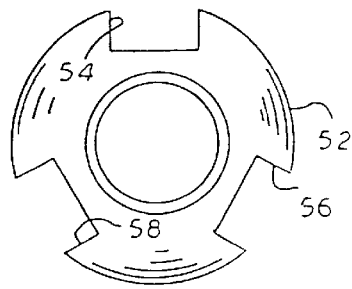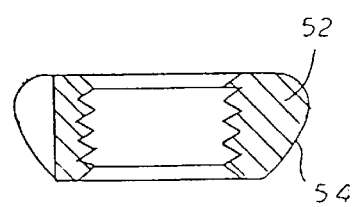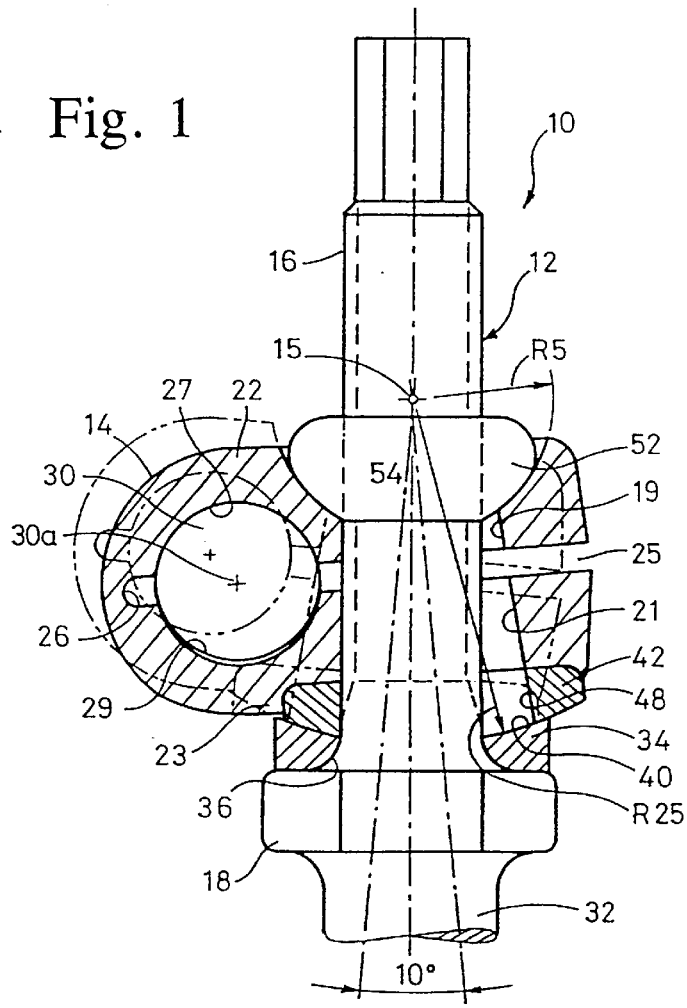

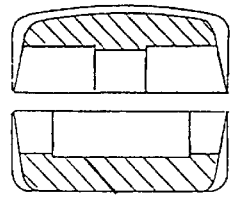
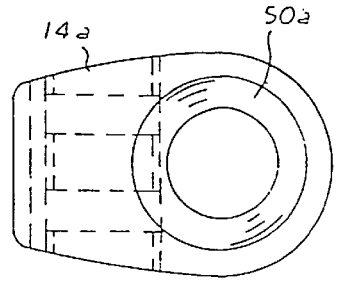
Fig. 5　　　Fig. 6
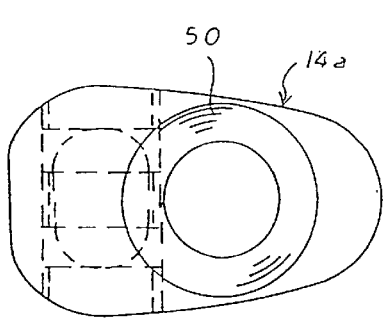
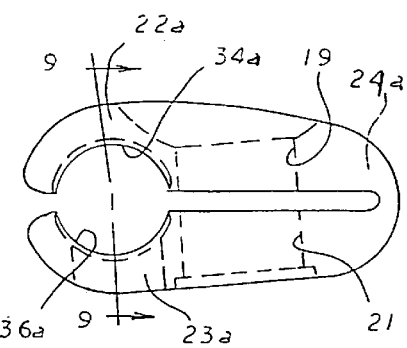
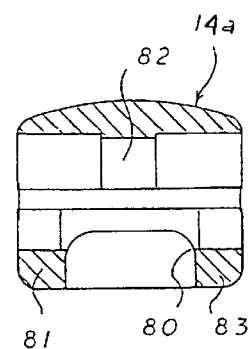
Fig. 7　　　Fig. 8　　　Fig. 9
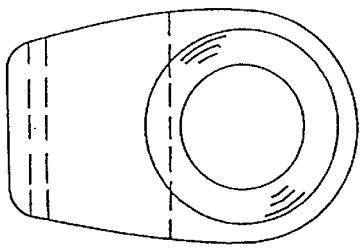
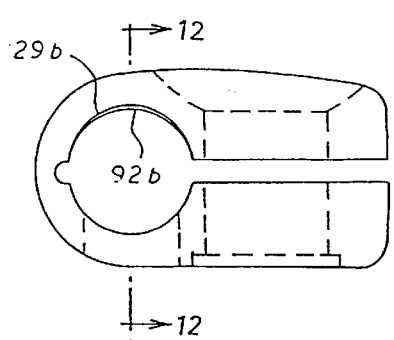
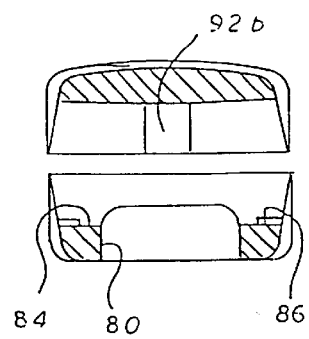
Fig. 10　　　Fig. 11　　　Fig. 12

6,123,706

APPARATUS FOR STABILIZING CERTAIN VERTEBRAE OF THE SPINE

FIELD OF THE INVENTION

The invention relates to an improved support system for stabilizing the spine during and after surgical treatment of spinal problems, which necessitates fixation of the spinal components with respect to one another.

Mechanisms are known whose aim is to stabilize the spine after surgical treatment of spinal problems. Many of these mechanisms included rods positioned parallel to the spine that carry pedicle screws via a connector. For instance, U.S. Pat. Nos. 4,433,676 and 4,369,769 are illustrative. Also, the Howland patents 4,653,481 (issued Mar. 31, 1987) and 5,030,220 (issued Jul. 9, 1991) are directed to fixation methods. Howland recognized the advantages of using a rod or shaft about which a pedicle screw carrying member can slide near the area of a selected vertebrae. An elongated slot in the connector permits a further adjustment.

In all spinal operations the skill of the surgeon is constantly challenged. The repair and reconstruction work that must be done is located close to vital nerve centers and each patient's spine is different in some respects.

In order for the healing to take place, it is oftentimes required to fix one vertebrae with respect to an adjacent or remote vertebrae.

The mechanism of this invention will fixedly secure to vertebrae together that are on either side of the injured portion of the spine. The vertebrae must be restrained from rotation or left to right, back to front, or up and down motions with respect to one another. substituted for discs and vertebras. The spine components are fixed in space with respect to one another until fusion occurs.

SUMMARY OF THE INVENTION

A principle objective of this invention is to provide a means by which pedicle screws can be readily adjusted and fixed along the length of a rod. It is essential that such longitudinal movement of the rod can be quickly accomplished with a mechanism that has few parts and which can be readily locked into position. This objective of this invention is met by providing a one-piece C-clamp that has a jaw at one end thereof which can be quickly and efficiently tightened about a smooth rod.

A still further objective of this invention is to provide a connector or clamp to carry a pedicle screw along the rod for coarse positioning and having a means to permit a pivoting movement between the pedicle screw and the connector for fine adjustment while maintaining a fixed reference distance between the rod and the pedicle screw pivot point at all times.

Another objective of the invention is to provide a one-piece clamping member having two opposed arms having a bore therethrough that permits relative pivoting movement between the connector and the pedicle screw for a fine adjustment while maintaining a fixed distance between the pivot point of the pedicle screw and the spinal rod.

A still further objective of the invention is to provide a pedicle screw clamping member which can be snapped or placed on a smooth rod and is locked or clamped into position via a three area contact by the same members that secure the pedicle screw to the clamping member.

Another principle objective is to provide a clamping assembly that permits the location of the clamping jaws in various locations in the connector and still preserve the same pivoting ability.

Another important objective of the invention is to provide a unique washer assembly that permits the connector to pivot with respect to the pedicle screw after the latter is screwed to a vertebrae.

The organization and operation of the invention described together with the objects and advantages thereof will be better understood from the following description considered in connection with the accompanying drawings in which the preferred embodiment of the invention is illustrated by way of example. It is to be expressly understood, however, that the drawings are for purposes of illustration and description only and not intended as the definition or limit of the invention.

BRIEF DESCRIPTION OF THE DRAWINGS

FIG. 1 is an exploded side elevation of several components of this invention;

FIG. 2 is a side view partially in section, of the components shown in FIG. 1 in their assembled relationship;

FIG. 3 is a top plan view of a clamping snap-nut washer;

FIG. 4 is a cross-section view of a washer along the line 4—4 of FIG. 2;

FIG. 5 is a cross-section along the line 6—6 of FIG. 1;

FIG. 6 is a top view of the member of FIG. 5;

FIG. 7 is a top plan of second embodiment of a connector;

FIG. 8 is a side view of the member of FIG. 7;

FIG. 9 is a cross-section along the lines 9—9 of FIG. 8;

FIG. 10 is a top plan of a third clamping member;

FIG. 11 is a side view of the member of FIG. 10;

FIG. 12 is a cross-section along the line 12—12 of FIG. 11;

DESCRIPTION OF THE PREFERRED EMBODIMENT

Figure 13:
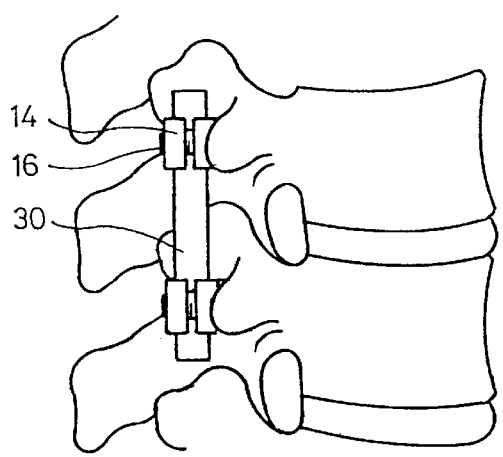
FIGS. 13 and 14 are overall views showing the relationship of the apparatus with respect to the spinal cord.

Referring now to the drawings wherein like numerals indicate like parts, the apparatus of this invention is generally indicated by the numeral 10. A pedicle screw assembly 12 is carried by a clamp or connector assembly 14 which permits pivoting about point 15. When the invention is actually in use by the surgeon it is the connector that pivots. In FIG. 2, the movement of the clamp with respect to the pedicle screw is shown.

The pedicle screw assembly 12, from top to bottom (as viewed in FIGS. 1 and 2), consists of a threaded portion 16; a curvilinear shoulder 17, a hexagonal nut 18, and a cancellous thread pedicle portion 20 for engagement with the vertebrae. The pedicle screw assembly 12 is received by openings 19 and 21 formed in the C-shaped clamp member 14. These openings are normally coaxial and will sometimes be referred to collectively just as openings 19. Also, the C-shaped clamp 14 will sometimes be referred to as connector 14.

The clamp or connector 14 is comprised of an upper arm 22 and a lower arm 23. The arms 22 and 23 are joined by an arcuate hinge section 24 which is integral with the arms 22 and 23. In the embodiment shown in FIG. 1, the arms 22 and 23 are formed with opposing jaws 27 and 29 to grasp a smooth round spinal stabilizing rod 30. In the embodiment of FIGS. 1 and 2, the jaws are formed near the hinged end 24. A lateral groove 25 is sometimes found in hinge section 24 to make the hinged end 24 more flexible. The connector 14 has its co-axial openings 19 and 21 formed in arms 22 and 23 to receive the pedicle screw assembly 12. The center axis 32 of the openings 19 and 21 is generally perpendicular to the arms 22 and 23.

In operation, pedicle screw members 14 are screwed into the pedicle bone section of vertebrae above and below the damaged area. The stabilizing rod 30 extends there between. The components associated with a single pedicle screw are described herein.

A washer 34 is slipped over the pedicle screw. Washer 34 has lower peripheral convex surface 36 matching the concave surface 17. The spinal stabilizing rod 30 has an axis 30a perpendicular to the center axis 32 of openings 19 and 21. A space 25 is defined between arms 22 and 23. As is well known in the art, pedicle screw holders or clamps are adapted to receive such spinal stabilization rods. The rod 30 is permitted to slide longitudinally with respect to the pedicle screw assembly prior to tightening. The pedicle screw portion 20 is threaded into the pedicle bone of a selected vertebrae. As will be seen hereinafter, the nuts and washers that secure the pedicle screw assembly 12 within the openings 19 and 21 and to the clamp 14 also move the arms 22 and 23 toward one another for clamping the connector to the rod 30. After the rod 30 is located and secured to the screw assembly, the arms are drawn together.

Arm 22 is formed with a jaw member 27 and the arm 23 is formed with a jaw member 29. When these jaws are located near the hinged end of the clamp as seen in FIG. 1 and 2, the clamp is sometimes referred to as a ring type clamp.

Once the clamping member 14 is located correctly with respect to the rod 30, the connector is permitted to pivot to permit the surgeon to position the rod 30 correctly with respect to the pedicle screw. This relative adjustment can be seen best in FIG. 2.

As seen in FIG. 2, the lower washer 34 is slipped over the upper end of the assembly 12 and is moved to a position where its curved surface 36 rests against the upper curved surface 17 adjacent the hexagonal nut 18. The washer 34 has a peripheral upper concave surface 40. The washer 34 remains longitudinally stationary with respect to the pedicle screw. A second washer 42 is then slipped over the assembly 12 until it engages washer 34. Washer 42 has a bottom convex surface 45 for engagement with the concave surface 40. These surfaces can slide with respect to one another about a center point with the interengaging surfaces forming an arcuate segment of a circumference defined by R-25.

The washer 42 can thus tilt and slide from side to side with respect to the lower washer 34. The washer 42 has a center opening 48 that is an extension of the openings 19 and 21 of arms 22 and 23.

Opening 19 in upper arm 22 of the connector is formed with an exterior concave counter bore 50. This annular depression or counter-bore 50 is formed at the upper end of opening 19. The counter-bore 50 is adapted to receive a star-nut 52 having a lower matching convex surface 54 in sliding engagement with the concave counter bore 50. These surfaces slide along an arc of radius R-5. The perimeter of snap-nut washer 52 is formed with notches 54, 56 and 58. These notches receive a three-pronged tightening tool whose hollow handle can slide over the threaded screw section 12 of the assembly 14 with its tines or prongs entering the notches 54, 56 and 58. The three pronged tool is not shown but such tools are known to the art. The snap-nut washer 52 is formed with a threaded opening 53 adapted to engage the threads of pedicle screw section 16.

It should be noted that the interior openings 19 and 21 are flared outwardly from counter bore 50 so as to permit the connector or assembly to pivot about point 15 in all directions. The surfaces of openings 19 and 22 form a continuous frustro-conical shape that theoretically extends across opening 25 between arms 22 and 23. The center openings 47 of the washers are also a continuation of that frustro-conical shape.

Operationally, the surgeon first threads the pedicle screws into the pedicle section of selected vertebrae. The hexagon 18 is used for that purpose. There will be at least two pedicle screws secured to the pedicle bones of vertebrae above and below the damaged bone o disc. The surgeon will then slip rod 30 through the jaws and locate them so that the connector and washers are located as seen in FIG. 2. When the rod 30 is so positioned, the jaws are tightened.

The pivotal screw assembly 12 has a fixed distance between center axis 34 of the rod 30 and the pivot point 15. However, relative pivoting movement between the elements is permitted so that the rod can be located in the desired position. The star nut 52 is then tightened along threads 12 until the rod 30 is securely grasped.

In the clamp shown in FIGS. 1 and 2, the clamping jaws are formed near the hinged end 24 of the clamp rather than at the distal ends of the arms.

One example of a distal end clamp is shown in FIGS. 7, 8 and 9. Here, the clamp or connector member is indicated by the numeral 14a. The clamp is formed by two arms 22a and 23a having jaw members 34a and 36a formed at the distal ends thereof. The openings 19a and 21a are formed respectively in the upper and lower arms 22a and 23a between the jaw members and the hinged area 24a. The clamp 14a is formed with a convex counter-bore 50 to receive the lower concave surface of a star-nut washer 52a, in the same manner as that shown in the previously described embodiment. The jaws 34a and 36a, of course, receive the spinal rod 30 in the same manner as the ring type connector previously described. Note that the lower jaw 36a is formed with an opening 80 forming bifurcated support extensions 81 and 83. Upper jaw member 34a of arm 22a has an interior arcuate ridge 82 intermediate its length. This ridge 82 and the surfaces 84 and 86 of the bifurcated extensions 81 and 83 provide a three-point suspension for rod 30.

Another ring type clamp is seen in FIGS. 10, 11 and 12. The upper jaw 29b is equipped with an arcuate ridge 92b and an opening 80 provides surfaces 84 and 86. This arrangement also provides the three-point suspension when the clamp is drawn together about spinal rod 32.

As mentioned previously, one of the goals of this invention is to establish with certainty a fixed distance between the axis of the spinal rod 32 and the pivot point 15. The systems herein described, however, permit a pivoting movement of the connector about screw assembly so that the surgeon can maneuver the rod to its most desirable location with respect to the spine and with respect to the previously secured pedicle screws.

The relative pivoting motion of the connector 14 with respect to pedicle screw assembly is seen by the dotted lines of FIG. 2. After the rod is properly located and the surgeon is satisfied with its location, the aforementioned three-pronged tool is utilized to tighten the nut 52. This causes the arms 22 and 23 to draw together about the rod. The snap nut and the sliding washers of each embodiment permit the limited pivoting movement (approximately 10° in the embodiment shown) of the connector 14 while maintaining the fixed distance between the pivoting point 15 and the center longitudinal axis of the rod 32.

Figure 14:
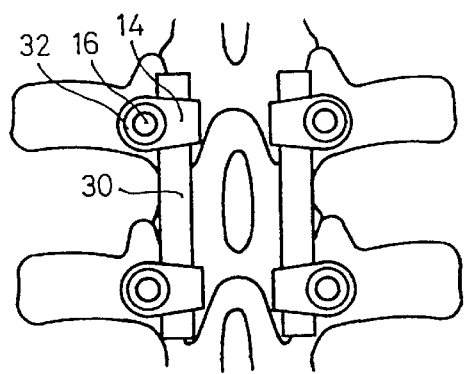

FIGS. 13 and 14 illustrate the relationship of the two rods 30 with respect to a spine A. The rods 30 fixedly secure two vertebrae B and C together and restrain them from rotation and other motions with respect to one another.

Figure 15:
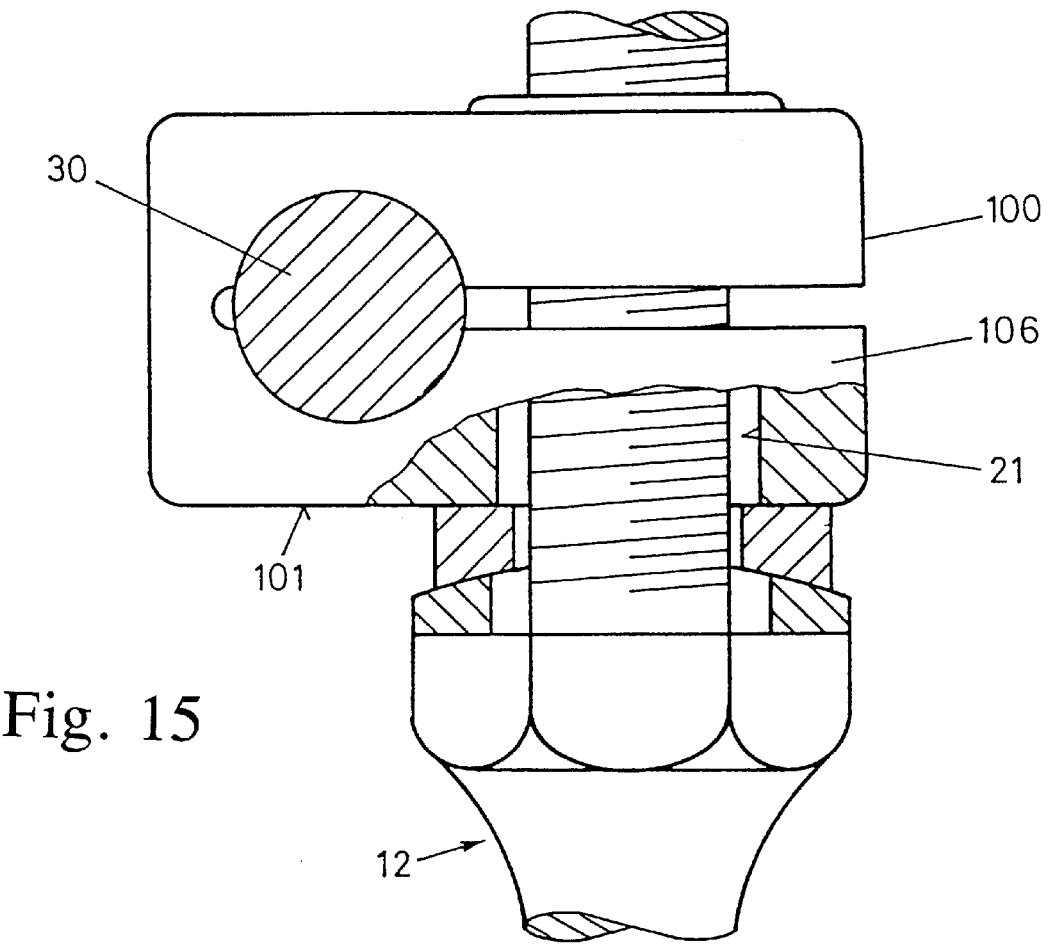
FIG. 15 is a side view partially in section of a further embodiment of the apparatus according to the invention.
Figure 16:
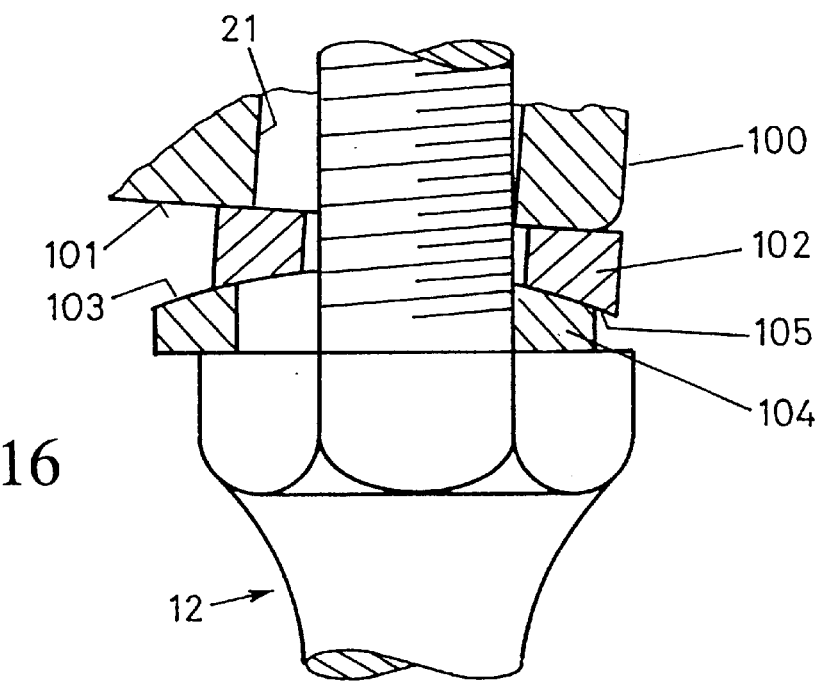
FIG. 16 illustrates the pivoting movement between the clamp and the screw.

Another embodiment of the apparatus is seen in FIGS. 15 and 16. The connector 100 has a lower arm 106 which does not have a recess underneath but a lower and planar surface 101 engaging a slip washer 102 with a concave surface 105 facing away from the connector 100. There is a second slip washer 104 having a corresponding convex surface 103 touching the concave surface 105 of the other washer 102. As FIG. 16 illustrates, the surfaces 103 and 105 permit a pivoting movement between the pedicle screw 12 and the connector 100 for fine adjustment while maintaining a fixed distance between the rod 30 and the pedicle screw. Biomechanical tests have proved that this embodiment was stronger in some applications and had more range of motion.

Figure 17:
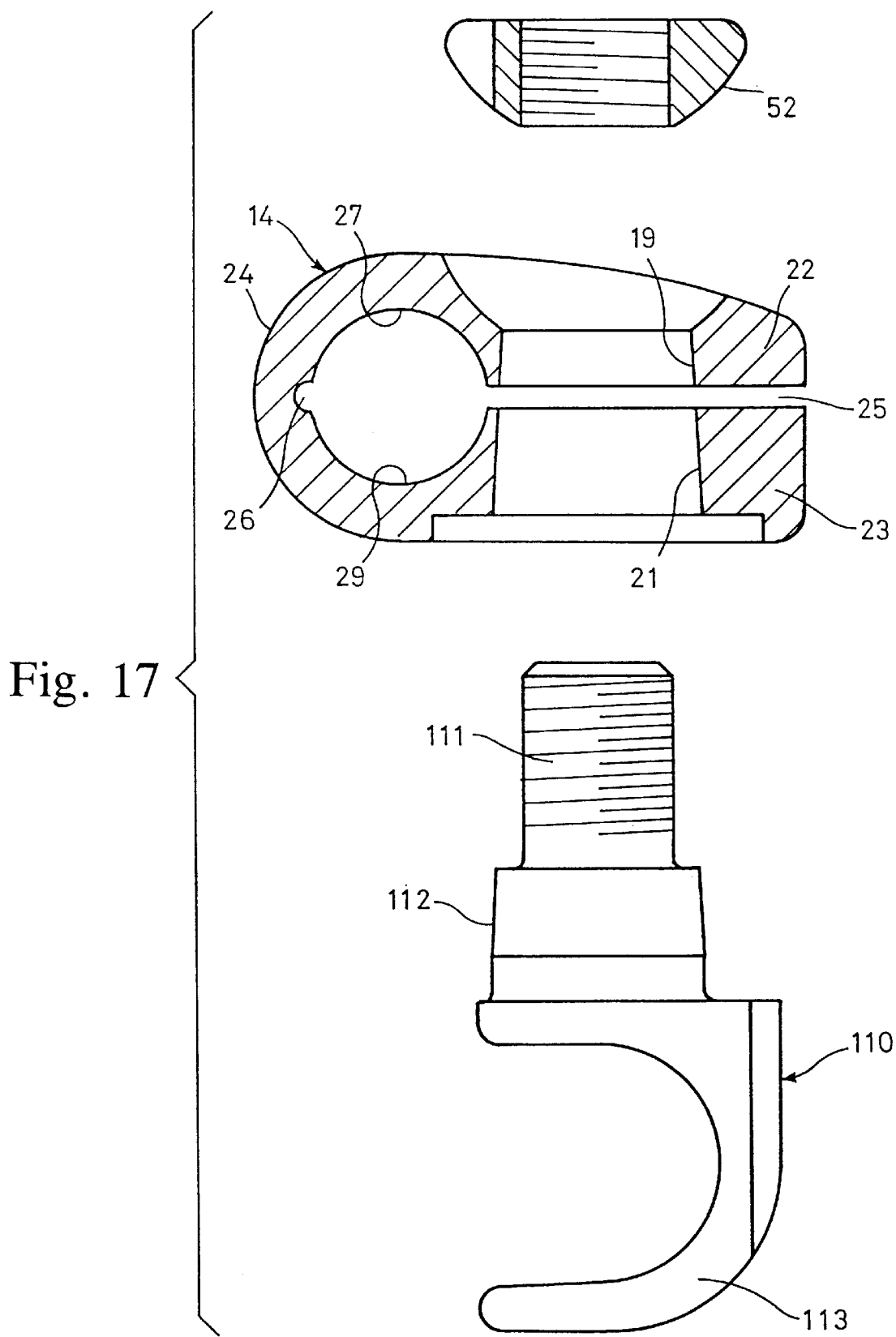
FIG. 17 is an exploded side elevation of a modular element and components of this invention.

The clamping member 14 and the nut 52 permit the surgeon to connect instead of the screw 12 a modular element 110 having at one end a hook part 113, as shown in FIG. 17. This modular element 110 is preferably an integral part of the system. The element 110 has at one end a thread portion 111 receiving the nut 52. When tightening the nut 52, a conical surface 112 touches the corresponding conical surface of opening 21.

Although the embodiments have been described with a certain degree of particularity, it is understood that the present disclosure has been made only by way of example and that changes in the details of construction and the combination and other arrangement of parts may be resorted to without departing from the spirit and scope of the invention. Thus, the scope of the invention should not be limited by the foregoing specification, but rather, by the scope of the claims appended hereto.

What is claimed is:

1. An apparatus for stabilizing certain vertebrae (B,C) of the spine (A) with respect to one another in a portion of the spine to be treated, the apparatus comprising:

a spinal stabilizing rod (30) that is adapted to be placed in a generally parallel relationship with the portion of the spine (A) to be treated;

a pedicle screw (12) including a bone cancellous type thread section (20) at one end thereof, a machine thread section (16) at another end thereof, and a nut portion (18) therebetween;

a connector (14) including a first arm (22) having a first opening (19) therethrough, a second arm (23) generally parallel to said first arm (22) and having a second opening (21) co-axial with said first opening, and a hinge coupling said arms (22, 23), said arms (22, 23) defining a space (25) therebetween;

said openings (19, 21) having dimensions greater than a cross-section dimension of said pedicle screw (12);

a mechanism (40, 42, 52) adapted to affix said pedicle screw (12) in said at least one of said first opening and said second opening, in a position about a pivot point (15) that remains fixed with respect to said rod (30) and permits said connector (14) to pivot with respect to said screw (12);

wherein said pivot point (15) is situated above a plane passing through a center axis (30*a*) of the stabilizing rod and the space (25) between the first arm and the second arm, the pivot point being on a same side as the machine thread section.

2. The apparatus of claim 1 wherein first and second arms (22, 23) respectively carry first and second jaws (34*a*, 36*a*) to receive said rod.

3. The apparatus of claim 2, wherein said first arm (22) is counter-bored about said first opening (19) to include an arcuate surface, and comprising a nut (52) threadedly received by said machine thread section (16) and including a lower surface matching and engaging said arcuate surface.

4. The apparatus of claim 3 where said nut (52) and said portion nut (18) of said screw (12) can tighten said jaws (22*a*, 23*a*) about said rod (30) when said nut (52) is threaded toward said hexagonal nut (18).

5. The apparatus or claim 1 wherein said rod (30) is adapted to receive two or more of said connectors (14).

6. The apparatus of claim 5 wherein each of said connectors (14) include upper and lower arms (22, 23) having opposing jaws (22*a*, 23*a*) at one end and a hinge (24, 24*a*) at the other end and said connector (14) is formed of one piece of material.

7. An apparatus for stabilizing certain vertebrae (B,C) of the spine (A) with respect to one another in a portion of the spine to be treated, the apparatus comprising:

a spinal stabilizing rod (30) that is adapted to be placed in a generally parallel relationship with the portion of the spine (A) to be treated;

a pedicle screw (12) including a bone cancellous type thread section (20) at one end thereof, a machine thread section (16) at another end thereof, and a nut portion (18) therebetween;

a connector (14) including a first arm (22) having a first opening (19) therethrough, a second arm (23) generally parallel to said first arm (22) and having a second opening (21) co-axial with said first opening, and a hinge coupling said arms (22, 23), said arms (22, 23) defining a space (25) there between;

said openings (19, 21) having dimensions greater than a cross-section dimension of said pedicle screw (12);

a mechanism (40, 42, 52) adapted to affix said pedicle screw (12) in said at least one of said first opening and said second opening, in a position about a pivot point (15) that remains fixed with respect to said rod (30) and permits said connector (14) to pivot with respect to said screw (12);

wherein said rod is adapted to receive two or more of said connectors (14);

wherein each of said connectors is formed of one piece of material, and wherein in each of said connectors (14), the first arm and the second arm comprise opposing jaws (22*a*, 23*a*) at a first end thereof and a hinge (24, 24*a*) at a second end thereof;

wherein one of said jaws (36*a*) is formed with a pair of ridges (84, 86) and the other of said jaws (34*a*) is formed with a single ridge (82, 92*b*) so that said rod (30) has a three point suspension.

8. The apparatus of claim 7 wherein said single ridge (82, 92*b*) is located in a plane intermediate the planes of said pair of ridges (84, 86).

9. An apparatus for stabilizing certain vertebrae (B,C) of the spine (A) with respect to one another in a portion of the spine to be treated, the apparatus comprising:

a spinal stabilizing rod (30) that is adapted to be placed in a generally parallel relationship with the portion of the spine (A) to be treated;

a pedicle screw (12) including a bone cancellous type thread section (20) at one end thereof, a machine thread section (16) at another end thereof, and a nut portion (18) therebetween;

a connector (14) including a first arm (22) having a first opening (19) therethrough, a second arm (23) generally parallel to said first arm (22) and having a second opening (21) co-axial with said first opening, and a hinge coupling said arms (22, 23), said arms (22, 23) defining a space (25) there between;

said openings (19, 21) having dimensions greater than a cross-section dimension of said pedicle screw (12);

a mechanism (40, 42, 52) adapted to affix said pedicle screw (12) in said at least one of said first opening and said second opening, in a position about a pivot point (15) that remains fixed with respect to said rod (30) and permits said connector (14) to pivot with respect to said screw (12);

wherein said second arm includes a lower surface (101) being a planar surface engaging a slip washer (102) with a concave surface (105) facing away from the connector.

10. The apparatus of claim 9 wherein said slip washer (102) engages a second slip washer (104) having a convex surface (103) touching the concave surface (105) of the other washer (102).

11. A system comprising an apparatus for stabilizing certain vertebrae (B,C) of the spine (A) with respect to one another in a portion of the spine to be treated, the apparatus comprising:

a spinal stabilizing rod (30) that is adapted to be placed in a generally parallel relationship with the portion of the spine (A) to be treated;

a pedicle screw (12) including a bone cancellous type thread section (20) at one end thereof, a machine thread section (16) at another end thereof, and a nut portion (18) therebetween;

a connector (14) including a first arm (22) having a first opening (19) therethrough, a second arm (23) generally parallel to said first arm (22) and having a second opening (21) co-axial with said first opening, and a hinge coupling said arms (22, 23), said arms (22, 23) defining a space (25) there between;

said openings (19, 21) having dimensions greater than a cross-section dimension of said pedicle screw (12);

a mechanism (40, 42, 52) adapted to affix said pedicle screw (12) in said at least one of said first opening and said second opening, in a position about a pivot point (15) that remains fixed with respect to said rod (30) and permits said connector (14) to pivot with respect to said screw (12);

including at least one modular element (110) wherein the modular element (110) includes at one modular end said machine thread section (111) and at another modular end a hook part wherein said mechanism is adapted to affix said modular element in said at least one of said first opening and said second opening (113).

12. System of claim 11 wherein the modular element (110) has an outer conical surface (112) corresponding to an conical surface of opening (21).

* * * * *